(12) United States Patent
Don Michael

(10) Patent No.: US 9,622,846 B2
(45) Date of Patent: Apr. 18, 2017

(54) APPARATUS AND PROCEDURE FOR TRAPPING EMBOLIC DEBRIS

(71) Applicant: Don Michael International, LLC, Bakersfield, CA (US)

(72) Inventor: T. Anthony Don Michael, Bakersfield, CA (US)

(73) Assignee: Don Michael International, LLC, Bakersfield, CA (US)

( * ) Notice: Subject to any disclaimer, the term of this patent is extended or adjusted under 35 U.S.C. 154(b) by 0 days.

(21) Appl. No.: 14/353,165

(22) PCT Filed: Oct. 19, 2012

(86) PCT No.: PCT/US2012/061038
§ 371 (c)(1),
(2) Date: Apr. 21, 2014

(87) PCT Pub. No.: WO2013/059603
PCT Pub. Date: Apr. 25, 2013

(65) Prior Publication Data
US 2014/0249572 A1    Sep. 4, 2014

Related U.S. Application Data

(60) Provisional application No. 61/594,669, filed on Feb. 3, 2012, provisional application No. 61/548,972, filed on (Continued)

(51) Int. Cl.
*A61F 2/01* (2006.01)
*A61F 2/24* (2006.01)

(52) U.S. Cl.
CPC .......... *A61F 2/013* (2013.01); *A61F 2/2436* (2013.01); *A61F 2/24* (2013.01); *A61F 2002/018* (2013.01);
(Continued)

(58) Field of Classification Search
CPC .......... A61F 2/01; A61F 2/013; A61F 2/2436; A61F 2002/011; A61F 2002/015;
(Continued)

(56) References Cited

U.S. PATENT DOCUMENTS 5,957,949 A * 9/1999 Leonhardt ................. A61F 2/07
606/108
6,932,830 B2    8/2005 Ungs
(Continued)

FOREIGN PATENT DOCUMENTS

WO    2004052239 B2    6/2004

*Primary Examiner* — Diane Yabut
*Assistant Examiner* — Martin T Ton
(74) *Attorney, Agent, or Firm* — Browdy and Neimark, PLLC

(57) ABSTRACT

A collapsible and deployable filter for blocking debris and passing blood in a blood vessel in a patient's body, the filter including; a framework of a flexible material, constructed to have a radially compressed state, in which the framework is radially compressed by radial deforming forces, and a radially expanded state to obdurate an artery; and a flexible filter material secured to said framework and having pores dimensioned to prevent the passage of debris therethrough while allowing the passage of blood. The filter has, in the radially expanded state of the framework, a generally conical or frustoconical form with a large diameter end, a small diameter end opposite to the large diameter end, and a side surface extending between the ends. The filter has an opening that is free of filter material at the small diameter end or in the side surface.

18 Claims, 13 Drawing Sheets

Related U.S. Application Data on Oct. 19, 2011, provisional application No. 61/648,311, filed on May 17, 2012, provisional application No. 61/701,126, filed on Sep. 14, 2012.

(52) U.S. Cl.
CPC . *A61F 2230/008* (2013.01); *A61F 2230/0067* (2013.01)

(58) Field of Classification Search
CPC ......... A61F 2002/018; A61F 2002/016; A61B 17/221; A61B 2017/2215
USPC .......................................... 606/114, 127, 200
See application file for complete search history.

(56) References Cited

U.S. PATENT DOCUMENTS

| | | | |
|---|---|---|---|
| 2001/0049486 A1* | 12/2001 | Evans | A61M 1/3621 604/4.01 |
| 2002/0123761 A1 | 9/2002 | Barbut et al. | |
| 2005/0137696 A1* | 6/2005 | Salahieh | A61F 2/013 623/2.11 |
| 2006/0015136 A1* | 1/2006 | Besselink | A61F 2/013 606/200 |
| 2006/0100658 A1 | 5/2006 | Obana et al. | |
| 2007/0213765 A1 | 9/2007 | Adams et al. | |
| 2008/0269877 A1* | 10/2008 | Jenson | A61F 2/013 623/2.11 |
| 2010/0185179 A1* | 7/2010 | Chan | A61B 17/3478 604/508 |
| 2013/0079731 A1* | 3/2013 | Chomas | A61M 25/0043 604/264 |

\* cited by examiner

APPARATUS AND PROCEDURE FOR TRAPPING EMBOLIC DEBRIS

BACKGROUND OF THE INVENTION

The present invention relates to an apparatus and procedure for aiding medical treatments in the blood circulation system of a patient, and in particular for preventing the circulation of embolic debris, or blood clots, resulting from such treatments. The invention is primarily, but not exclusively, concerned with providing protection in connection with procedures like those for implanting a prosthetic heart valve.

There are known procedures, known as transcatheter aortic valve implantation (TAVI), in which a prosthetic heart valve is implanted at the site of a defective native valve, or of a previously implanted defective prosthetic valve. In these procedures, the new prosthetic valve and its guiding structure are introduced by a transcutaneous catheterization technique. For example, for implanting a prosthetic aortic heart valve, the valve and delivery components will be introduced through an incision in the groin or arm and along a blood vessel path to the desired location.

Such a procedure is disclosed, for example, in U.S. Pat. No. 7,585,321, which issued to Alan Cribier on Sep. 8, 2009, the entire disclosure of which is incorporated herein by reference. Such valves and their associated guiding devices are marketed by Medtronic and by Edwards Lifesciences, one example of the Edwards valves being marketed under the trade name Sapien.

Although such prosthetic valves have been used successfully to provide a replacement for stenotic native heart valves or defective prosthetic valves, the implantation procedure can result in the creation of embolic debris, which will flow downstream through the circulatory system and will, in a certain percentage of cases, cause blockages in smaller blood vessels.

BRIEF SUMMARY OF INVENTION

The present invention provides an apparatus and procedure to prevent the circulation of embolic debris resulting from procedures carried out in the blood circulatory system, one such procedure being, for example, the implantation of a prosthetic heart valve.

To this end, the invention provides a novel filter and a novel combination of such filter and a blocking device for trapping embolic debris produced during such a medical procedure. It also provides the filter with a central, or axial, orifice through which the valve implantation device, or system, can be directed, which facilitates this process and reduces the traumatic effects of the valve implantation device on the wall of the aorta. Since it is known that trauma to the aortic wall generates clots and calcium, the position of the orifice in the filter acts as a landmark and facilitates atraumatic entry of the valvular device.

The invention also provides, together with the filter and blocking device, a stent or stent graft that is preliminarily deployed against the inner wall of the blood vessel, e.g., the aorta, to prevent trauma during introduction of the filter.

In further accordance with the invention, the filter can be delivered in, deployed from and retracted into, a known radially expandable sheath provided particularly to facilitate retraction of the filter.

The components of embodiments of the invention may be conveyed to the treatment site along various blood vessel paths and may all be introduced via the same path or via respectively different paths. For example, if the components are to be positioned in, or pass through, the aorta, the, or each, component can be introduced through an incision in a groin and the associated femoral artery, or through an incision in an arm and the associated subclavian artery.

DETAILED DESCRIPTION OF THE INVENTION

Figure 1:
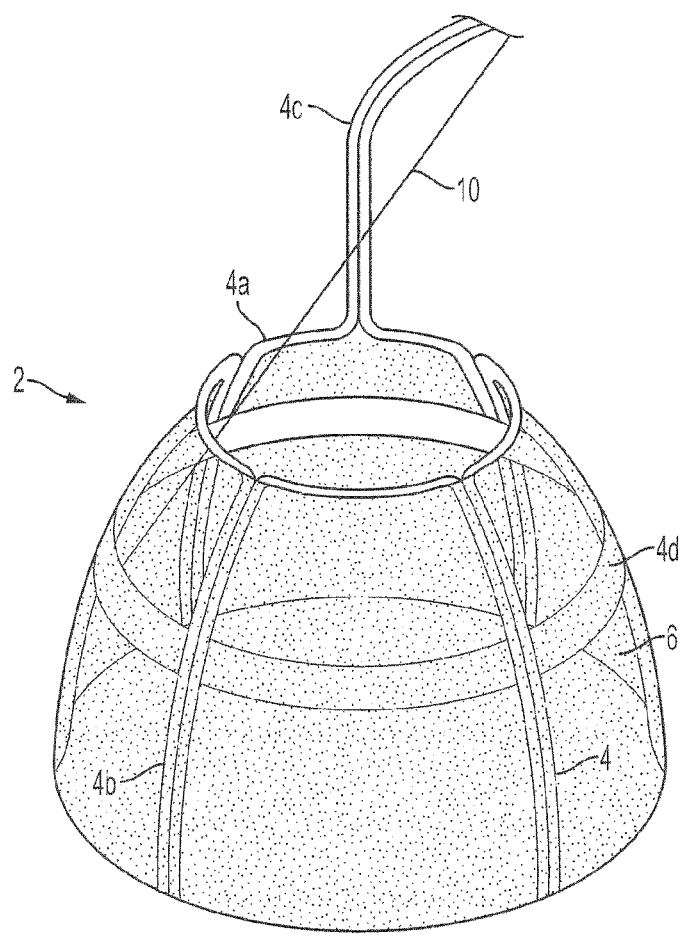
FIG. 1 is a perspective view of an embodiment of a filter according to the present invention.

FIG. 1 illustrates one embodiment of a filter 2 according to the invention composed of a wire framework 4, made of a memory metal such as nitinol, and a filter fabric 6 of appropriate pore size, supported by a framework 4.

Filter 2 has a generally cylindrical structure with a small diameter end, at the top in FIG. 1, and a large diameter end, at the bottom in FIG. 1. In the expanded state of filter 2, the diameter of the small diameter end can be in the range of 18-26 mm and the maximum diameter of the large diameter end can be of the order of 35 mm.

According to a presently preferred embodiment of the invention, the large diameter end of filter 2 is formed to have a generally oval shape with a major diameter of about 40 mm and a minor diameter of the order of 30 mm. This allows the lower end of the filter to better conform to the somewhat oval shape of a normal aorta.

Of course, the dimensions of filter 2 can be varied to conform to aortas having different sized, for example in children.

Filter 2 has a form defined by an outwardly bowed arcuate generatrix of rotation about the longitudinal axis of filter 2 such that the wall of the filter bows outwardly, as shown in FIG. 1.

The framework of the illustrated embodiment is composed of a single wire that includes a ring 4a at the small diameter end, a series of longitudinal struts, or ribs, 4b, and a control portion 4c that extends to a location outside of the patient's body to allow the position of filter 2 to be controlled by medical personnel. The framework further includes a circumferential band 4d at a location between the small diameter end and the large diameter end. The framework may also include a circular or oval nitinol ring extending around the large diameter end and bonded to the lower ends of ribs 4b.

Filters composed of a framework of memory metal, e.g. nitinol, wires can be constructed to present a radial expansion/compression ratio of 8:1, or more. Therefore, they will be deployed in a sheath or tube having an inner diameter preferably equal to or greater than ⅛ the desired expanded diameter of the large diameter end of the filter.

Figure 2:
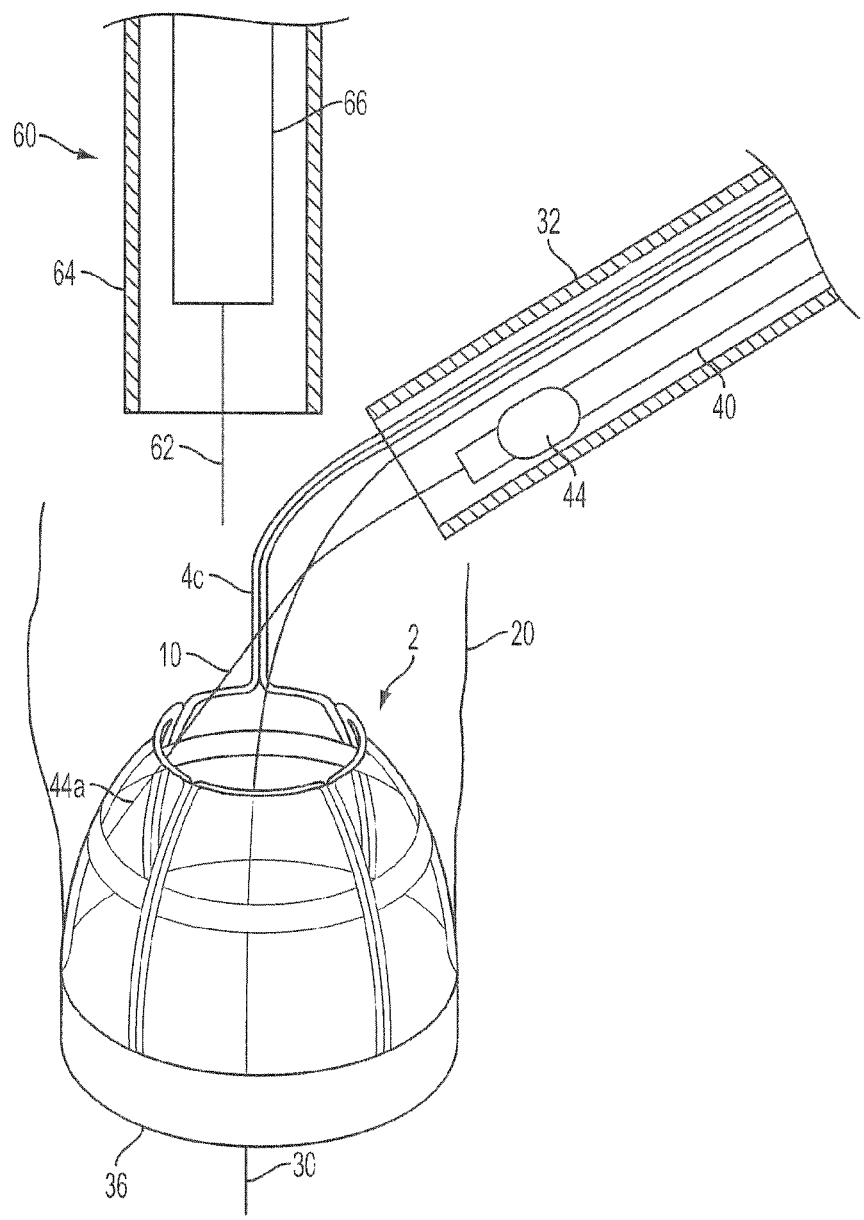
FIG. 2 is a perspective and partly cross-sectional view of the filter shown in FIG. 1, together with related components and a heart valve delivery system.

While FIG. 2 shows the framework to be provided with six ribs 4b, a filter framework in accordance with the present invention can have many other configurations and can, for example, be provided with a larger number of ribs 4b. The framework can also be made of individual wires that are soldered or otherwise secured together. In addition, control portion 4c can be a single wire or can be composed of two, four, or more wires, each connected to ring 4a at a respective location such that the wires are distributed, preferably at uniform intervals, around ring 4a.

The structure shown in FIG. 1 further includes a guidewire 10 having a distal end soldered or otherwise secured to the interior surface of band 4d. The purpose of guidewire 10 will be explained below with reference to FIG. 2.

Filter fabric 6 can be of any medically acceptable material having appropriate mechanical properties and pore size suitable for trapping debris while allowing the passage of blood therethrough. Examples of suitable materials for the framework and the filter fabric are described in, for example, U.S. Pat. No. 7,214,237, the entire disclosure of which is incorporated herein by reference.

FIG. 2 illustrates all of the components of a system for implanting a prosthetic aortic heart valve while preventing the passage of embolic debris.

The components shown in FIG. 2 will be described in conjunction with a description of the manner in which they are used.

In FIG. 2, filter 2 is shown in position in the patient's aorta 20 with the base, or large diameter end, of filter 2 located close to the defective aortic valve 36.

The apparatus associated with filter 2 includes a guidewire 30 that is introduced transcutaneously and then along a blood vessel path into the aorta and through the center of the native or previously implanted heart valve. Guidewire 30 is then used to guide the introduction of a sheath, or tube, 32 along the same blood vessel path and into aorta 20 to bring the distal end of sheath 32 adjacent the existing valve. During introduction, filter 2 is collapsed within sheath 32. Then, when sheath 32 has been brought into the desired position in aorta 20, for example adjacent the interface between the aorta and the existing heart valve, guidewire 30 can be withdrawn and sheath 32 can be withdrawn, at least by a distance to not interfere with the valve implantation procedure, while filter 2 is held in place by acting on control portion 4c, or the plural control wires, from outside the patient's body so that filter 2 is freed from sheath 32. Filter 2 is thus automatically deployed, or expanded, and placed in the position and configuration shown in FIG. 2, where the large diameter end of filter 2 is preferably downstream of the coronary artery entrances to assure that blood flow to those arteries will not be impeded by debris accumulating on fabric 6.

Sheath 32 also contains a catheter 40 provided at its distal end with a low compliance, or noncompliant, blocking balloon 44. Catheter 40 also includes, in a conventional manner, a balloon inflation lumen in communication with balloon 44. Catheters provided with such lumens are well known in the art. One example being U.S. Pat. No. 7,169,171, the entire disclosure of which is incorporated herein by reference. Catheter 40 may have a diameter as small as 4 Fr. (1.3 mm).

After filter 2 has been deployed, catheter 40 is advanced along guidewire 10 to bring balloon 44 to the location 44a shown in broken lines in FIG. 2. At this time, balloon 44 may be partially of fully deflated. After balloon 44 has been brought to position 44a, it may be partially inflated by introduction of a radioactive contrast, or radiopaque, fluid, the purpose of which will be described below.

At a time after filter 2 has been deployed, guidewire 30 and sheath 32 can be withdrawn from the patient's body.

Then, an assembly 60 for implanting the prosthetic heart valve is introduced into the aorta, preferably, but not necessarily, via a different blood vessel path, by first passing a guidewire 62 along that blood vessel path through the center of filter 2 and through the existing heart valve. Assembly 60 includes, in addition to guidewire 62, a sheath, or tube, 64 and a system 66 including the prosthetic heart valve and components for deploying it After guidewire 62 is put in place, tube 64 is introduced into the aorta over guidewire 62 to a location adjacent filter 2, after which system 66 is extended out of tube 64 and through ring 4a of filter 2 and along the central orifice defined by filter 2, for implanting the prosthetic heart valve. System 66 and one suitable manner in which it is used to implant a prosthetic heart valve are all described in detail in U.S. Pat. No. 7,585,321, the entire disclosure of which is incorporated herein by reference.

Valve assembly 60 can be inserted by puncturing an artery in the groin and advancing it upwards through the femoral artery and the aorta, followed by advancing system 66 through the existing valve. Alternatively, the valve assembly can be inserted by puncturing the heart at its apex and deployed from a location below the existing valve. The valve assembly could also be introduced through either the right or left subclavian artery, which normally supplies the upper extremity. Consequently, there is the option of introducing sheath 32 and filter 2 through either subclavian artery or through the femoral artery. In general, it is presently preferred to use one of these paths, the subclavian artery or femoral artery, for introducing sheath 32, and the other of these paths for valve assembly 60. Since sheath 32 can have a smaller diameter, it might be advantageous to advance it through the subclavian artery path.

The filter shown in FIG. 2 and described above may be provided with an opening and a catheter identical to elements 88 and 89, shown in FIG. 6, which will be used in the manner described with reference to FIG. 6.

If elements 88 and 89 are provided, then, after filter 2 has been deployed at the desired location, for example in the aorta, a guide wire will be introduced through the groin into filter through opening 88, which is surrounded by a nitinol ring, followed by introduction of catheter 89 over the guidewire and into filter 2 to bring the distal end of catheter 89 adjacent to the aortic valve, after which the guidewire may be withdrawn. Catheter 89 may have a diameter of 5-6 Fr. Catheter 89 is then used both to flush contrast and visualize the valve, and at the end of the procedure to drain debris. Catheter 89 is retained in filter 2 until the filter is closed and catheter 89 is withdrawn just prior to its entry of opening 88 into filter sheath 32, thus minimizing the leakage of debris into the blood stream. After withdrawal, opening 88, which is molded to a nitinol strut of filter 2, will lie within the exit through the filter sheath.

The procedure described above with reference to catheter 89 is to be used if the TAVI valve assembly 66 and filter 2 are introduced through the subclavian artery.

It is presently believed to not be desirable to use the same route for introducing both assemblies due to the fact that every trial done so far has criticized the valve assembly alone as being relatively thick and traumatic in the process of puncturing the artery. The only acceptable single route, which is not favored by patients, is to puncture the heart. For all these reasons, the diameter of valve assembly 60 has been reduced in Europe to 18 mm, although this is not yet approved by the USFDA.

It is important to note that the valve assembly is a cylindrical, relatively rigid structure below which the valve hangs, crimped on an angioplasty balloon, and that expansion of the valve is produced by inflating the angioplasty balloon in the case of the Edwards device and by pulling on the valve using nitinol bands in the case of a Medtronic device.

Neither of these techniques interferes with the use of the filter assembly according to the present invention, which serves to isolate the carotids and other parts of the blood circulatory system from debris that is released during and after implantation of the prosthetic valve, regardless of which valve implantation technique is used.

During implantation of the heart valve, tube 64 can bear against the opening at the top of filter 2 to help prevent the passage of embolic debris. Filter 2, sheath 32 and wire 10 are oriented to cause wire 10 to extend into filter 2, adjacent ring 4a, at a location to not interfere with the positioning of tube 64.

Balloon 44 may be partially inflated with radioactive contrast fluid before withdrawal of the components 66 for implanting the heart valve and tube 64; and immediately after withdrawal of those components, balloon 44 is further inflated, if this was not previously done, and pulled back by acting on catheter 40 from outside the patient's body to cause balloon 44 to block the small diameter opening of filter 2. The presence of radioactive contrast fluid allows the position of balloon 44 to be monitored fluoroscopically.

Inflated balloon 44 acts to close the smaller diameter hole in filter 2 as soon as the prosthetic valve introduction system is retracted out of the filter, thus enabling debris to be trapped adjacent the smaller diameter end of the filter.

Then, after a suitable period of time has elapsed, during which debris can become trapped in filter 2, filter 2 and balloon 44 are drawn into sheath 32 by pulling on control portion 4c, or the plural control wires, if provided, and catheter 40 and tube 64, along with all of the associated components, are withdrawn from the patient's body.

More specifically, balloon 44 will remain inflated and lodged in the smaller diameter opening of filter 2 during an initial phase of withdrawal so that filter 2 and catheter 40 will be pulled toward sheath 32 as a unit. Then, when the smaller diameter end of filter 2 reaches sheath 32, balloon 44 will be deflated and catheter 40 may be partially or fully retracted so that balloon 44 moves out of contact with filter 2. Then, filter 2 can be retracted into sheath 32; and then sheath 32, containing catheter 40 and filter 2, can be fully withdrawn from the patient. During this withdrawal procedure, suction may be applied through sheath 32 to assist the removal of any embolic debris from filter 2.

As an alternative to using a wire 10 to introduce balloon catheter 40, it would be possible to simply use a small diameter catheter with a balloon at the end, surrounding the catheter wall and communicating with a balloon inflation lumen formed in the catheter, to close the opening, or orifice, at the top of filter 2 as soon as valve assembly 60 is pulled out of the filter, thereby preventing escape of emboli. This small diameter catheter may be introduced with the aid of a guidewire that extends though the catheter.

The fact that filter 2 is open at the top offers the advantage of preventing the filter from being blown out by the relatively forceful blood flow being produced by the heart as it pumps the blood.

The radiopaque fluid used to inflate balloon 44 will enable the balloon to be readily observed.

Inflated balloon 44 will also serve as a means for partially altering the configuration of the filter and making it parallel to and in line with sheath 32 to facilitate retraction of filter 2 into sheath 32 after completion of the procedure.

Figure 3:
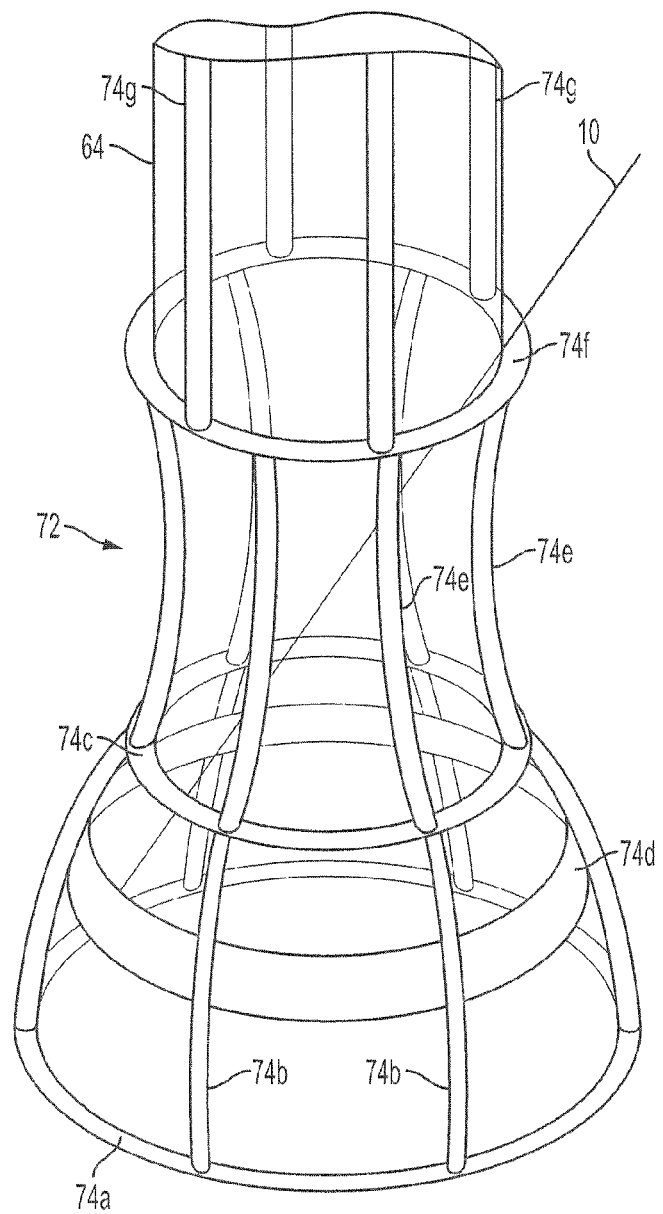
FIGS. 3 and 4 are views similar to those FIGS. 1 and 2 of a second embodiment of the present invention.
Figure 4:
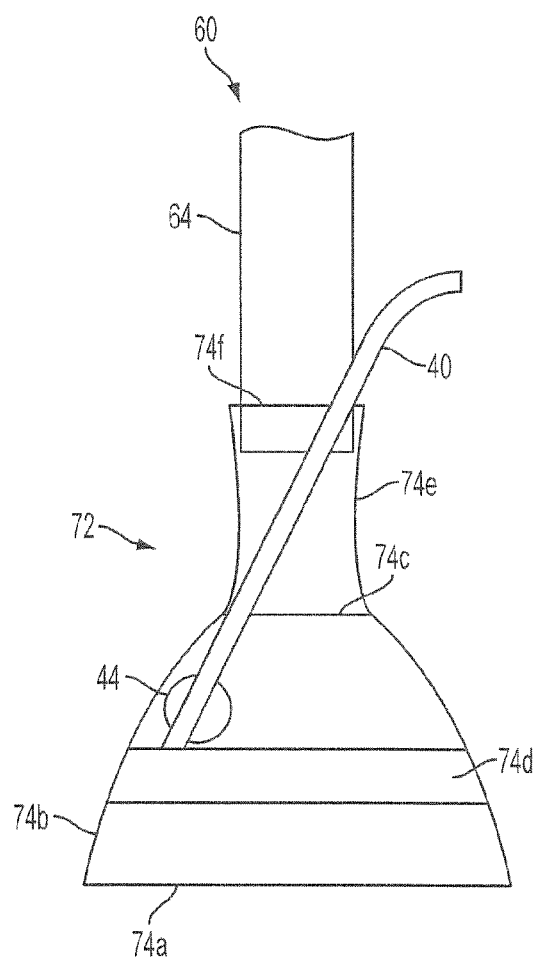

FIGS. 3 and 4 show a filter 72 according to a second embodiment of the invention that can provide improved protection against the escape of embolic debris. Filter 72 has a generally cylindrical structure, at least when expanded, and is composed of a framework presenting two portions: a lower portion between a ring 74a at the lower end of the filter and a ring 74c at the upper end of the lower portion; and an upper portion extending between ring 74c and a ring 74f at the upper end of the filter.

The lower portion is also composed of a series of longitudinal struts, or ribs, 74b extending between rings 74a and 74c, and a circumferential band 74d at a location between rings 74a and 74c. Preferably, as in the case of the embodiment of FIGS. 1 and 2, ring 74a is shaped so that in its expanded, or deployed, state, it has an oval form with major and minor diameters of the order of 40 mm and 30 mm, respectively.

Struts 74b, like struts 4b of FIGS. 1 and 2, are preformed to curve in the manner illustrated when the filter is deployed, in which case the external surfaces of struts 74b are outwardly convex.

The upper portion of filter 72, between rings 74c and 74f, is provided with a plurality of longitudinal struts, or ribs, 74e. Preferably, struts 74e curve in the opposite direction from struts 74d so that struts 74e are outwardly concave when the filter is deployed. However, struts 74e can also be constructed to have a straight form when the filter is deployed.

The framework of filter 72 is completed by, preferably, four wires 74g constituting a control portion performing the same function as control portion 4c shown in FIGS. 1 and 2. The provision of four wires 74g allows for the possibility of controlling the positioning of the filter in the aorta.

Like the embodiment shown in FIGS. 1 and 2, the filter shown in FIGS. 3 and 4 includes guidewire 10 whose distal may be soldered or otherwise secured to the inner surface of band 74d. The purpose of guidewire 10 is essentially the same of that of the guidewire 10 described with reference to FIGS. 1 and 2.

Also like the embodiment of FIGS. 1 and 2, a filter fabric is suitably secured to and supported by the framework composed of components 74a-74f. Also as in the case in the embodiment shown in FIGS. 1 and 2, there is no fabric in the planes enclosed by rings 74a and 74f.

Also shown in FIG. 3, in broken lines, is the distal end of tube 64. At least ring 74f is dimensioned to allow entry of tube 64 into the region enclosed by filter 72 and wires 74g. Ring 74f, in the deployed state of filter 72, could have a larger diameter than ring 74c if needed to accommodate tube 64.

Preferably, ring 74f is dimensioned to provide a close fit with tube 64. Optionally, the distal end of tube 64 can be slightly tapered to allow introduction of tube 64 into the upper portion of filter 72, while assuring the establishment of a tight fit with ring 74f, and possibly to provide a sealed connection between tube 64 and ring 74f, thereby preventing the escape of embolic debris from filter 72 during valve implantation.

The manner in which filter 72 is used will be explained with reference to FIGS. 2, 3 and 4.

Filter 72 is employed together with system 60, sheath 32, catheter 40 and low compliance or noncompliant balloon 44, all of which are shown in FIG. 2, and the operation of which has been described above.

After filter 72 has been installed and positioned to surround the entire region through which the replacement valve will be deployed, catheter 40 carrying balloon 44 is advanced over guidewire 10 to the location shown in FIG. 4 and tube 64 is introduced over guidewire 62 so that the distal end of tube 64 penetrates at least the upper part of the upper portion of filter 72, and preferably forms a seal with ring 74f. Tube 64 and catheter 40 essentially block the upper end of the upper portion of filter 72. Since catheter 40 has a relatively small diameter, of the order of 1 mm, only a minimal gap will exist at the top of upper portion of filter 72 so that escape of debris from filter 72 will be minimal, if any.

Then, system 66 is operated to install the replacement heart valve.

At the completion of this operation, after system 66 has been withdrawn back into tube 64, balloon 44 is at least partially inflated and catheter 40 is withdrawn to bring balloon 44 into contact with ring 74c. Before or after balloon 44 has been brought to the proper position, it may be further inflated in order to form a tight seal at the location of ring 74c. Then assembly 60 can be fully withdrawn, after which filter 72, with balloon 44 still in place and inflated, begins to be withdrawn into sheath 32 by pulling on control wires 74g.

After the top portion of filter 72 has been introduced into sheath 32, balloon 44 is deflated while, preferably, suction is produced within sheath 32 in order to withdraw any debris being held within filter 72.

After deflation of balloon 44, filter 72 and catheter 40 are completely withdrawn into sheath 32, and sheath 32 can then be withdrawn from the patient's body.

The invention as described above offers a number of other advantages. For example, it will allow injection of clot lysing material into the filter and if catheter 40 is provided with an orifice above filter 2, it can be used to continuously monitor the arterial blood pressure.

The filter disclosed herein may also be used to trap embolic debris, or blood clots, in other procedures, such as in treating children or young adults with congenital heart disease who have pulmonary stenosis and on whom is performed a similar procedure that may generate blood clots.

In FIGS. 2 and 4, a catheter carrying a blocking balloon and a tube 64 for the valve delivery system both pass through the opening at the top of the filter. While it is obvious that there will be a gap present around the catheter, the size of the gap would be no more than approximately 1/24 of the diameter of tube 64. However, in the case of filter 72, balloon 44 will form a near-perfect seal with ring 74c. both before the withdrawal of system 66 carrying the valve and thereafter. The technique would be to inflate the balloon at the junction with the valve carrying device and track both these structures upwards during their withdrawal. At a time not later than the point in the procedure when the valve delivery sheath is about to exit the bottleneck, the balloon would be fully expanded to completely close the orifice through which it is retracted, thereby preventing escape of emboli both in the early and late phases of valve/sheath withdrawal. When this is accomplished, and the sheath of the valve is separated from the bottle neck carrying the balloon, the correct procedure would be to advance sheath 32 carrying the bottleneck from the side arising from the subclavian artery and collapse the balloon and catheter into sheath 32. The balloon would have appropriate consistency which allows it to be optimally in contact with the nitinol sheath; if it is underinflated or has a low pressure it may not prevent emboli from going upwards between the balloon and nitinol sheath. If it is excessively stiff and high pressure, it could stretch and damage the nitinol filter.

Balloon 44 should be one with a reasonably low compliance such that it does not rupture and does not expand the bottle neck. which is preferably made of nitinol but has a firm surface.

The components of the embodiment shown in FIGS. 3 and 4 can be introduced into the aorta over the same paths as described with reference to the embodiment of FIGS. 1 and 2.

Figure 5:
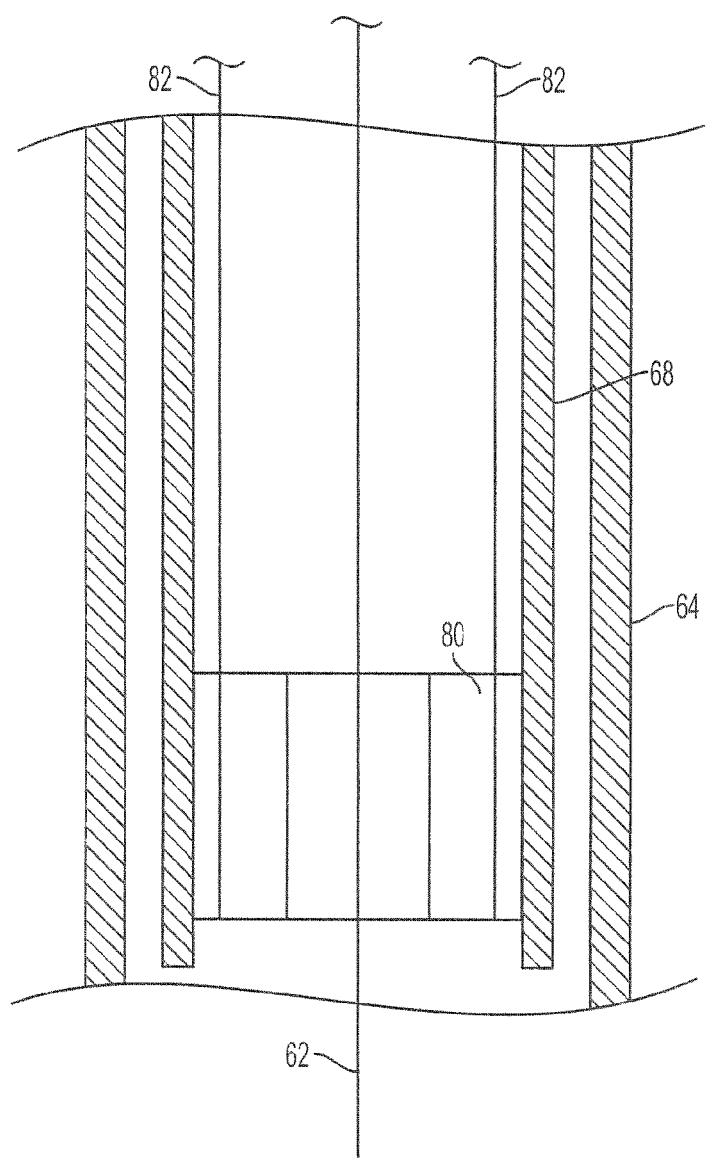
FIG. 5 is a cross-sectional view relating to a third embodiment of the invention.
Figure 6:
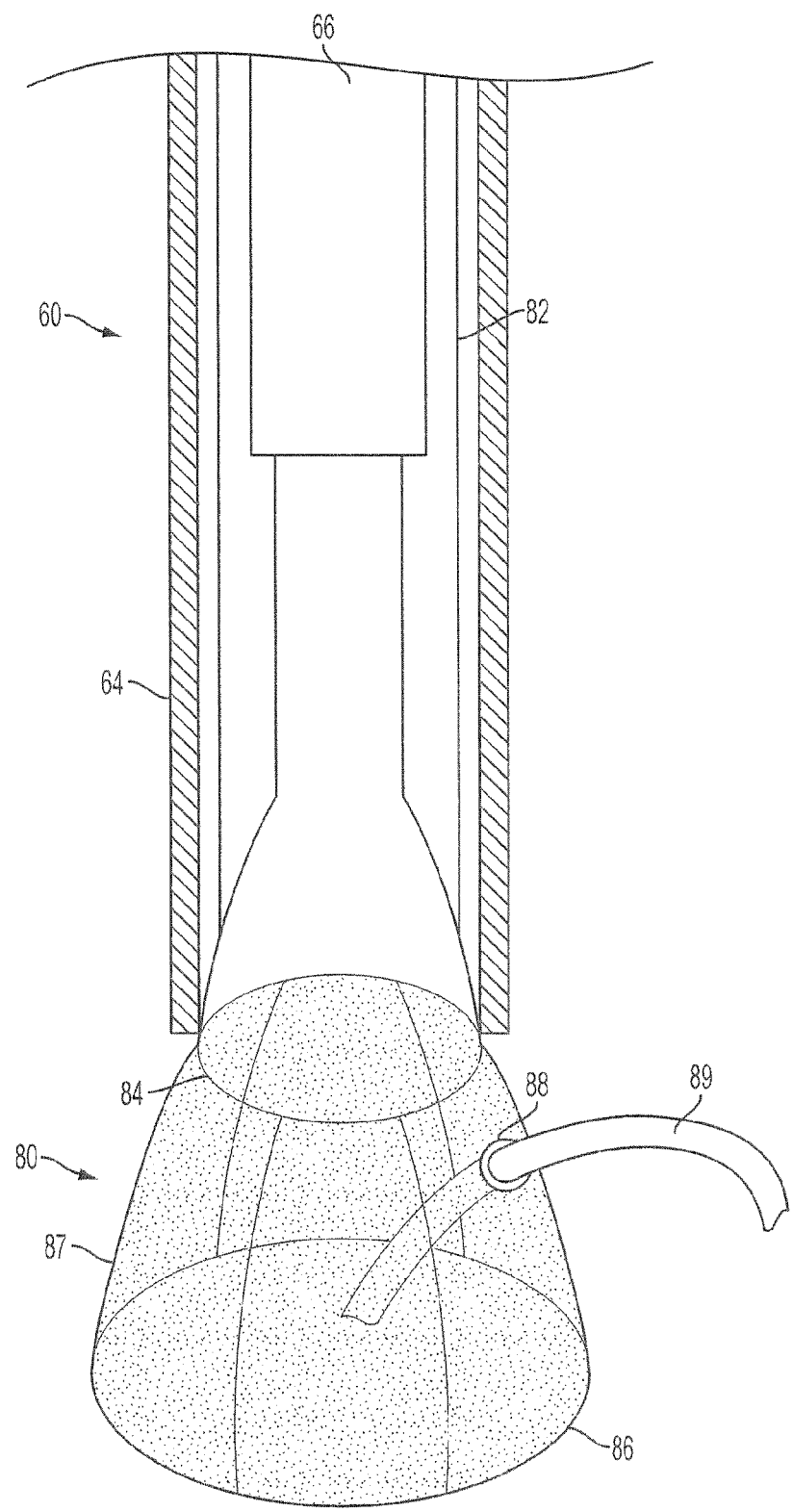
FIG. 6 is a view, partly in cross section and partly perspective, showing the third embodiment of the invention.

A further embodiment of the invention is shown in FIGS. 5 and 6.

According to this embodiment, components 60 and 80, to be described below, can be introduced along the same path, for example along the femoral artery and into the aorta via an incision made in the groin, or through one subclavian artery, as described earlier herein. Component 89 can be introduced along a path including the radial artery of one arm.

The components shown in FIG. 5 include a guidewire 62 that is introduced first into the ascending aorta (20 in FIG. 2), preferably to a point close to the valve that is to be replaced. Then, guidewire 62 is used to introduce a first sheath 64, which may have a diameter of the order 7 mm, and the distal end of sheath 64 is also brought to a point in the ascending aorta, after which guidewire 62 may be withdrawn, and a second sheath 68, which may have a diameter of the order of 6 mm, is introduced into sheath 64.

Sheath 68 contains a filter 80 somewhat similar to filter 2 shown in FIGS. 1 and 2. In the illustration provided in FIG. 5, filter 80 is held in a radially compressed state in sheath 68.

Filter 80, which will be described in greater details below with reference to FIG. 6, is provided with two control wires 82 that extend through sheath 68 to a location outside of the patient's body.

After sheath 64 has been brought to its desired position in the aorta, sheath 68 will be advanced to bring its lower, or distal, end to a location close to the defective heart valve, at least approximately where the lower end of filter 80 is to be deployed. Then, sheath 68 is retracted while filter 80 is held in place by acting on control wires 82. As filter 80 thus exits the lower end of sheath 68, the filter expands while it is being deployed to bring it to the desired position to collect debris.

Then, sheath 68 may be withdrawn from the patient's body.

Referring now to FIG. 6, which shows filter 80 in its deployed state, it will be seen that filter 80 is compose essentially of a framework that includes an upper ring 84, a lower ring 86 and longitudinal struts 87, all preferably made of a type of a memory metal such as nitinol. The sides of filter 80 are covered with a suitable filter fabric having a pore size of, for example, 110 μm. Filter 80 is open at the top and the bottom and has a generally frustoconical shape when deployed.

Filters having a nitinol frame can generally extend radially by a maximum factor of 8 and filter 80 is dimensioned so that in the deployed, or expanded state, lower ring 86 has a diameter of the order of 32 mm and upper ring 84 has a diameter of the order 7 mm. Sheath 64 is brought to a position in which, as shown in FIG. 6, the lower end of the sheath 64 contacts ring 84.

After filter 80 has been thus deployed and sheath 64 has been brought into the position shown in FIG. 6, a system 66, described earlier herein, will be introduced through sheath 64 and then through filter 80, after which system 66 will be operated in a known manner to implant the prosthetic valve.

Typically, introduction of system 66 will be aided by a guidewire such as guidewire 62 shown in FIG. 2 of the application drawing, which will be introduced in order to guide system 66 past the defective heart valve.

During implantation of the heart valve, debris will be released and this debris will be confined by filter 80 and will be carried off with blood through sheath 64 to a suction device located outside of the patient's body. This blood and debris can pass through at a conventional device such as a Coulter counter, which detects and counts the debris particles. Suction will be continued until the output of the measuring device indicates that no further debris is present in the blood flow.

After such an indication has been produced, filter 80 can be withdrawn, by acting on the control wires 82, into sheath 64 and all components can then be withdrawn from the patient's body.

The side of filter 80 is provided with a small diameter ring 88 secured to a strut 87. Ring 88 may be made of nitinol wire. Filter fabric is not present in the region enclosed by ring 88.

Ring 88 is dimensioned to receive a small diameter tube, or catheter, 89, which may have a diameter of the order of 5-7 Fr., preferably 5-6 Fr., and is preferably dimensioned to achieve a sufficiently close fit between ring 88 and tube 89 to prevent the escape of debris therebetween. Catheter 88 may be of a type known as a "pigtail" catheter.

After filter 80 has been deployed at the desired location, a guidewire (not shown) is introduced, for example through the groin or the subclavian, and then passed though ring 88 into the region enclosed by filter 80. Then tube 89 is passed over the guidewire and through ring 88, also into the region enclosed by filter 80.

Tube 89 is employed to inject a contrast fluid that facilitates visualization of the surgery site, such as the aorta and the aortic valve.

After the need to inject contrast fluid has ended, tube 89 can be pulled up so that its lower end is still within filter 80 and so that it continues to obturate the opening defined by ring 88. Tube 89 can be connected to a suction device outside the patient's body to suction debris, inevitably accompanied by blood, through tube 89. Outside of the patient's body, debris can be filtered out of the blood and the blood can be returned to the patient's circulatory system, as will be described subsequently herein.

Figure 7:
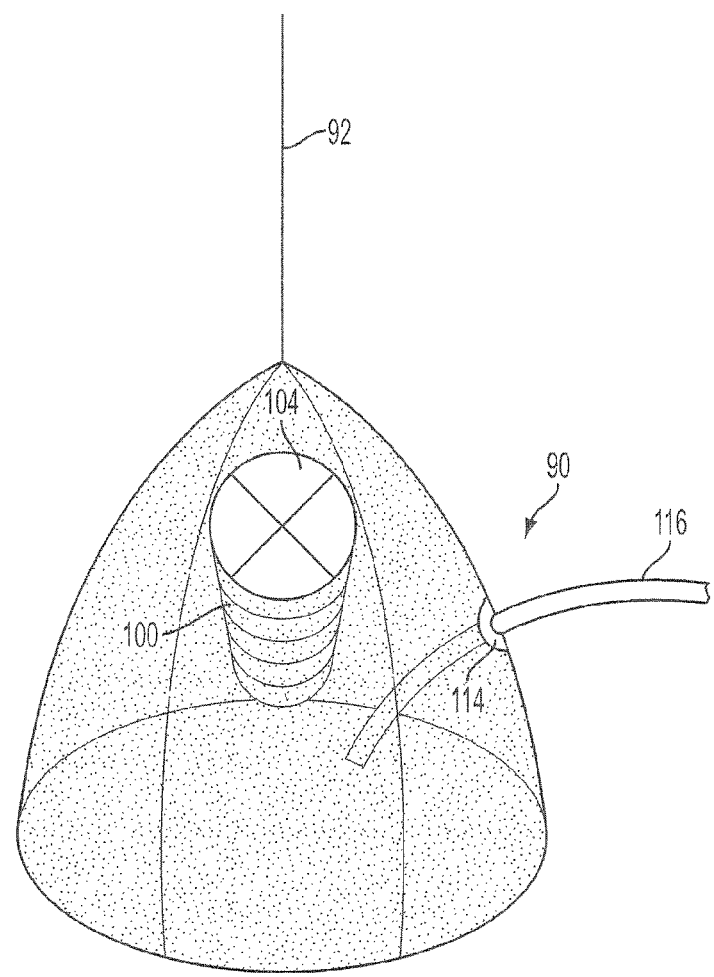
FIG. 7 is a perspective view relating to a fourth embodiment of the invention.
Figure 8:
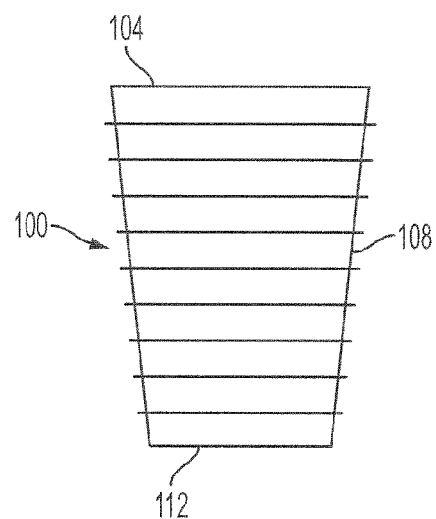
FIG. 8 is a detail view of a component of the fourth embodiment of the invention.
Figure 9:
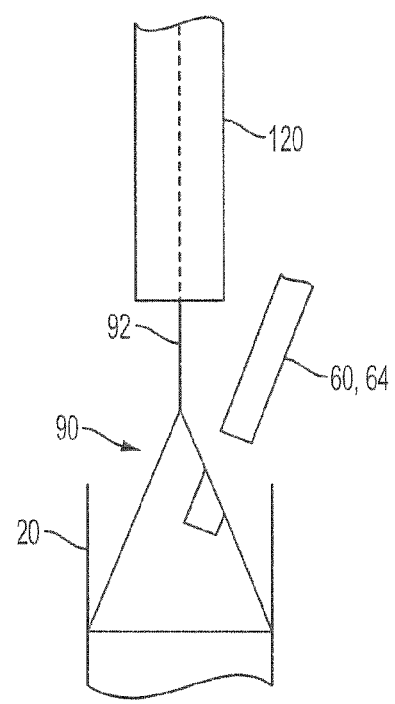
FIG. 9 is a pictorial view showing the fourth embodiment of the invention.

A further embodiment of the invention is illustrated in FIGS. 7, 8 and 9.

FIG. 7 shows a filter 90 having a general conical form that is open at its large diameter lower end, closed at its upper end, and the sides of which are covered with filter material, or fabric, filter 90 thus being in the general form of a cone.

Filter 90 is provided with a control wire 92 at its apex, where it is closed. Filter 90 can be introduced through a subclavian artery, for example the left suclavian artery.

Filter 90 is provided with an entry cone 100 and a side opening 104 in which filter fabric is not present. Side opening 104 is closed by a series of flaps of a suitable material, constructed to normally be closed. Cone 100 is composed of a tube 108, which may be corrugated, and which is open at its inner end 112, as shown most clearly in FIG. 8.

Filter 90 is provided with a further opening 114 for introduction of a catheter 116, such as a pigtail catheter. The structure and function of opening 114 and catheter 116 are the same as those of opening 88 and catheter 89, as described earlier herein with reference to FIG. 6.

Referring to FIG. 9, filter 90 is introduced into position in aorta 20 by means of a sheath 120 that performs essentially the same function as sheath 32 shown in FIG. 2, except, in this embodiment, components 40, 44 and 44a are not provided. After filter 90 has been deployed, essentially in the manner described earlier therein, assembly 60 is introduced, possibly through the femoral artery and the descending aorta, and is inserted into cone 100 through opening 104. Preferably, cone 100 is dimensioned so that at least the lower end thereof forms a seal with tube 64.

Then, in the manner described previously, for example with respect to FIG. 2, the guidewire associated with assembly 60 is introduced through the defective heart valve and assembly 60 is then operated to implant the new valve.

After implantation, suction is maintained through tube 64 to extract debris mixed with blood and, as in the case of the embodiment of FIGS. 5 and 6, the blood being suctioned is measured to determine when all debris has been removed.

Then, assembly 60 is withdrawn from the patient's body, filter 90 is retracted into sheath 120, and sheath 120, with retracted filter 90, is withdrawn from the patient's body.

In further accordance with the invention, a wall stent or stent graft may be initially deployed to protect the aorta during valve implantation and an inflatable sheath may be employed in place of sheath 32 to facilitate retraction of filter 2, 72, 80, 90. In addition, the filter may be provided with additional structures to control blood flow from the heart in a manner to assure that the filter is not displaced by the force of the blood flow. These features will be described in detail below.

Two well known stent-grafts are: the Cook Zenith Flex graft and the Medtronics graft for the ascending aorta.

In each embodiment of the invention, the framework may be coated or impregnated with radiopaque material, or could be provided with individual radiopaque studs, or beads, lining the top and/or the bottom rings of the filter framework to facilitate guidance of the filter to its desired position and introduction of wire 62. i.e. guidance of system 66 through the hole at the top of the filter and into the existing valve.

A significant advantage of filters according to the present invention is that they are constructed to surround the entire circumference of the valve that is deployed, with the result of preventing blood clots from entering the coronary arteries.

In the case of the embodiment shown in FIGS. 7, 8 and 9, sheath 120 may be introduced through one subclavian artery, assembly 60 may be introduced through a femoral artery and catheter 116 may be introduced through a radial artery or the other subclavian artery.

Figure 10:
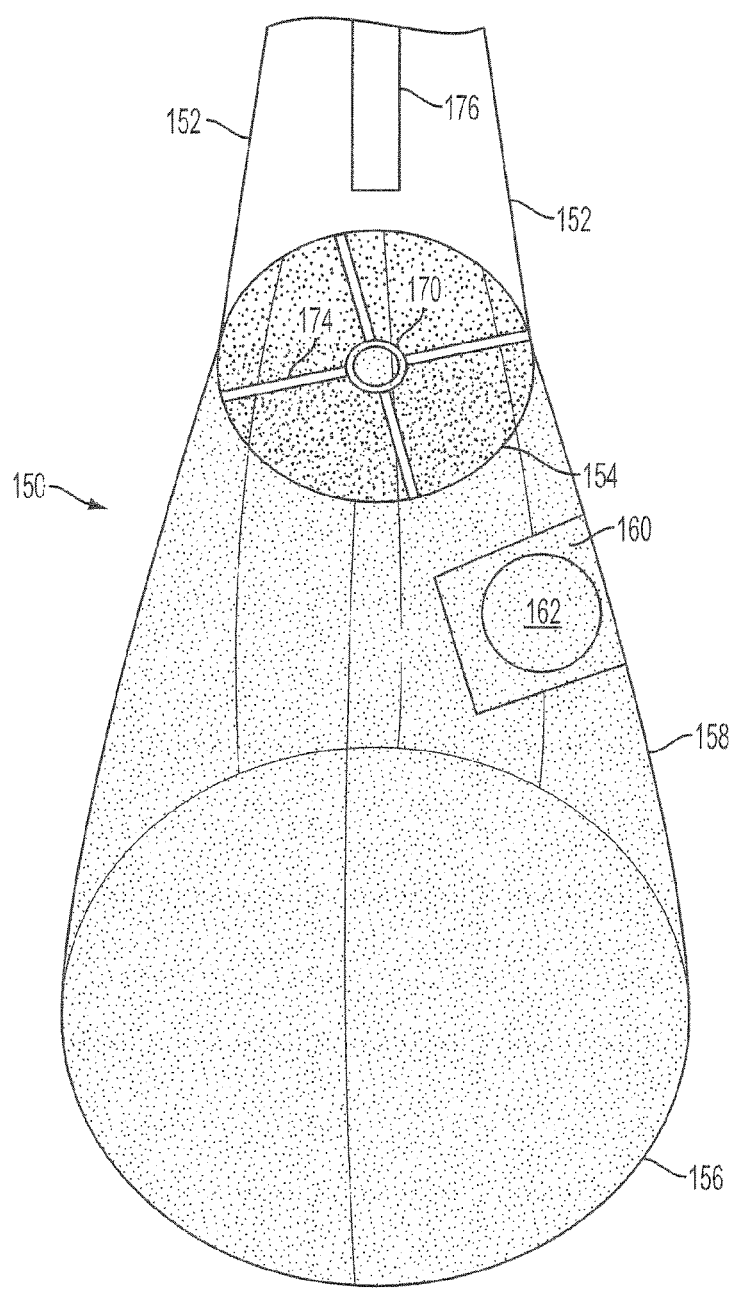
FIG. 10 is a perspective view of a further embodiment of a filter according to the invention.
Figure 11:
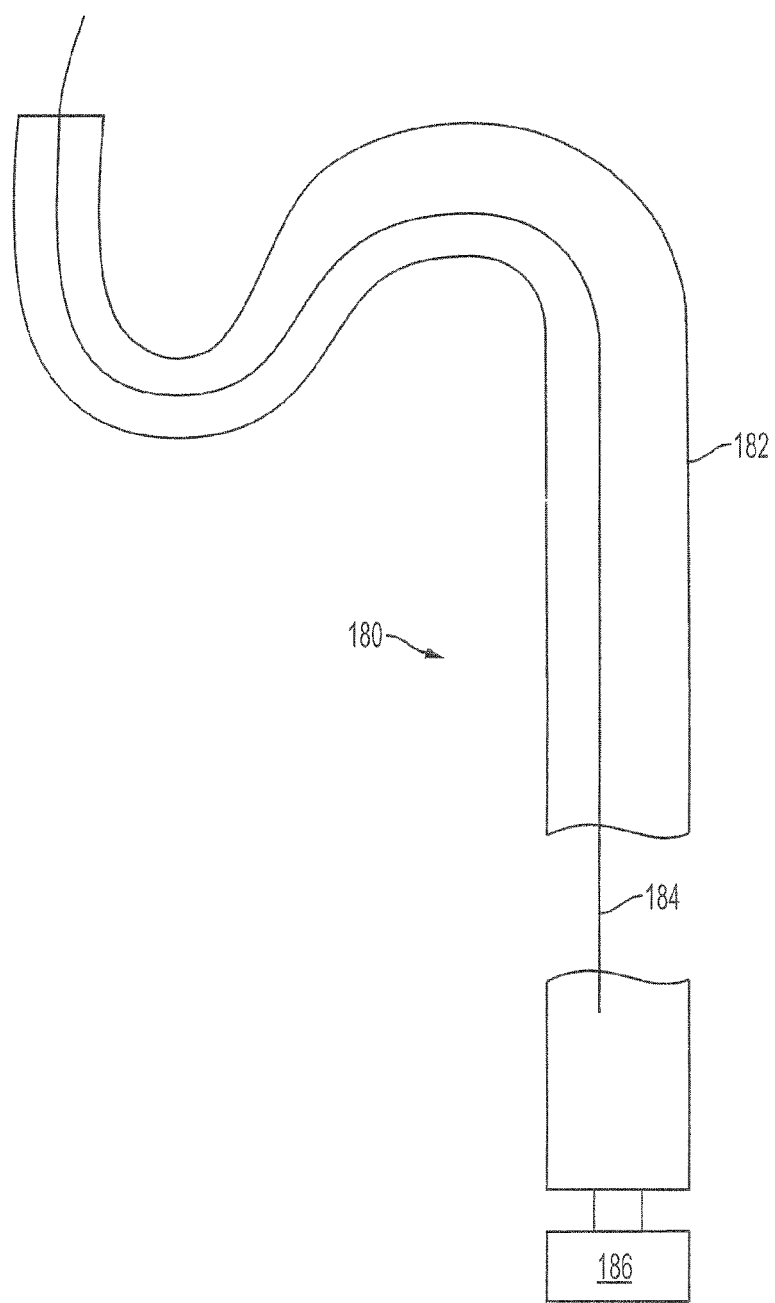
FIG. 11 is a pictorial view of a device employed with the filter of FIG. 10.

A further embodiment of the invention is composed of a debris filter 150, shown in FIG. 10 and a debris suction assembly 180, shown in FIG. 11.

The filter shown in FIG. 10 is somewhat similar to filter 80 shown in FIG. 6. Filter 150 is provided with control wires 152 corresponding in function to control wires 82 shown in FIG. 6. Filter 150 is composed of an upper ring 154, a lower ring 156 having, in a deployed state of the filter, a larger diameter than ring 154, and longitudinal struts 158, all of these parts preferably being made of a type of memory metal such as nitinol. Upper ring 154 is connected to wires 152. The sides of filter 150 are covered with a suitable filter fabric having a pore size of, for example, 100 μm, or more generally a pore size that will permit as free a flow of blood as possible, while retaining embolic debris within the filter.

The lower end of filter 150, enclosed by ring 156, is open to receive blood and debris from the region being treated, such as the heart valve region and the area of the aortic wall into which vein bypasses are customarily attached or implanted.

Filter 150 differs from filter 80 essentially only in that the upper end of filter 150, enclosed by ring 154, is covered with the same type of filter fabric as described earlier herein, with a pore size of, for example 100 μm. The upper end of filter 150 may be provided with a small diameter ring 170 secured to ring 154 by at least four radial spokes 174. The outer ends of spokes 174 are bonded to ring 154 in any suitable manner to secure ring 170 in place. Ring 170 and spokes 174 may be made of nitinol wires. Filter fabric is not present in the region enclosed by ring 170.

Ring 170 is dimensioned to receive a small diameter tube, or catheter, 176, which may have a diameter of the order of 5-6 Fr. and is preferably dimensioned to achieve a sufficiently close fit between ring 170 and tube 176 to prevent the escape of debris therebetween. Catheter 176 may be of a type known as a "pigtail" catheter.

After filter 150 has been deployed at the desired location, a guidewire (not shown) is introduced, for example along the same path as filter 150, and then passed though ring 170 into the region enclosed by filter 150. Then tube 176 is passed over the guidewire and through ring 170, also into the region enclosed by filter 150.

Filter 150 is provided at its side with a plate 160 provided with a through opening 162 that is not covered with filter fabric.

Tube 176 is employed to inject a contrast fluid that facilitates visualization of the surgery site, such as the aorta and the aortic valve. It can also be utilized to work with a TAVI catheter assembly which is inserted through opening 162. Thus, the catheter 176 and the TAVI catheter can be used simultaneously to permit observation of the natural valve and to cross it, respectively.

After the need to inject contrast fluid has ended, tube 176 can be pulled up so that its lower end is still within filter 150 and so that it continues to obturate the opening defined by ring 170. Tube 176 can be connected to a suction device outside the patient's body to suction debris, inevitable accompanied by blood, through tube 176. Outside of the patient's body, debris can be filtered out of the blood and the blood can be returned to the patient's circulatory system The debris suction assembly shown in FIG. 11 is composed of a suction tube 182 having, in its unstressed state, a form such as shown, where the distal end of tube 182 has a generally S-shaped configuration. The proximal end of tube 182, which will be located outside of the patient's body, is coupled to a suction device to aid in the removal of debris from filter 150.

Tube 182 is provided to be inserted through a blood vessel in order to cause its distal end to be inserted through opening 162 and brought into proximity to the upper end of filter 150.

The devices shown in FIGS. 10 and 11 are intended to be employed together with a valve implantation assembly, such as assembly 60 shown in FIG. 2 and described in detail earlier herein.

A procedure according to the invention, using the devices shown in FIGS. 10 and 11, along with a valve implantation assembly is performed in the following manner.

A first guidewire is inserted along a blood vessel path to a point close to the heart valve that is to be replaced and then a sheath, such as sheath 32 shown in FIG. 2, is advanced over the guidewire. Then, the guidewire is withdrawn and a filter 150 is introduced through and out of the sheath to a location corresponding to that shown in FIG. 2. The delivery of filter 150 is controlled by control wires 152. Filter 150 may be installed initially in the distal end of sheath 32, prior to introduction of sheath 32 into the blood vessel. If ring 170 is provided, the first guidewire cam be inserted through the hole enclosed by ring 170 prior to introduction into the blood vessel. If ring 170 and its associated hole are not provided, the first guidewire can be initially threaded through side opening 162 and then through the blood vessel Then, a second guidewire, such as guidewire 62 shown in FIG. 2, is introduced through a blood vessel path and directed through opening 162. Then, assembly 60 is introduced into the blood vessel path and tube 64 or system 66 is caused to pass through opening 162 and is operated to implant an artificial valve, as described above.

After the valve has been implanted, assembly 60 and guidewire 62 are removed from the patient's body.

As quickly as possible after removal of assembly 60, a third guidewire 184, shown in FIG. 11, is introduced through a blood vessel passage and through opening 162. Thereafter, tube 182 is advanced over guidewire 184 through opening 162 in order to bring the distal end of tube 182 close to the upper, small diameter, end of filter 150, the region enclosed by ring 154.

Then, guidewire 184 is withdrawn from the patient's body and tube 182 is allowed to assume approximately its unstressed state so that the inlet that terminates the distal end thereof is at the desired location, in proximity to, and pointing towards, the upper or apical portion of the filter 150, proximal to the opening to the filter an expandable balloon is used with traction applied against the nitinol molded orifice to prevent debris from leaking through this orifice which is larger than the catheter that is inserted.

Suction device 186 is placed into operation in order to suction debris, together with some blood, from the patient's body. The withdrawn fluid may be filtered to separate debris from blood and the blood can be returned to the patient's body, for example via a vein.

After a suitable period of time, assembly 180 and filter 150 are withdrawn.

All of the guidewires employed in the practice of all of the embodiments disclosed herein may be any commercially available guidewires intended for use in blood vessels, such as Charter™ Guidewires marketed by Navilyst Medical of Marlborough, Mass.

The following table lists the blood vessel passages that can be used for introduction of each of the devices described above.

| FIG. | DEVICE | ARTERY |
| --- | --- | --- |
| 2 | 32 | Subclavian |
| 2A | 32 | Subclavian |
| 5 | 62 | Subclavian |
| 6 (2A) | 32 | Subclavian |
| 7 | 92 | Subclavian or femoral |
| 9 | 60 | Femoral |
| 10 (2A) | 150 | Subclavian |
| 11 | 180 | Femoral |

If, in the procedure described with reference to FIGS. 10 and 11, the TAVI assembly and the filter sheath are introduced through the groin, the pigtail catheter can be introduced through the apex of the filter similar to that shown in FIGS. 10-13, in which the hole is located at the top of the filter in the central area within the upper ring of the filter.

It is important to point out that the TAVI catheter and the pigtail catheter are in proximity to each other prior to and immediately after the valve is implanted. This is an essential part of the procedure which ensures appropriate positioning during the process of implanting the valve. It is also to be noted that in either event, namely, using the subclavian or the groin, due to the constraints of space, the TAVI catheter assembly 60 and the filter enter through the same artery, with the filter sheath being withdrawn from the artery before introduction of the valve implantation assembly 60, while, the pigtail catheter is introduced through a different artery. This ensures that the diameter of the blood vessel in either case is not stretched to the point of injury.

In the case of the embodiment shown in FIGS. 10 and 11, filter 150, in its introduction sheath, may be introduced through a femoral artery or a subclavian artery, debris suction assembly 180 may be introduced through a femoral artery or subclavian artery different from that used for filter 150, the TAVI catheter assembly may be introduced through a femoral artery or subclavian artery different from those used for introducing filter 150 and assembly 180, or through the same artery as assembly 180 after that assembly has been removed. Catheter 1776 may be introduced through a radial artery.

Figure 12:
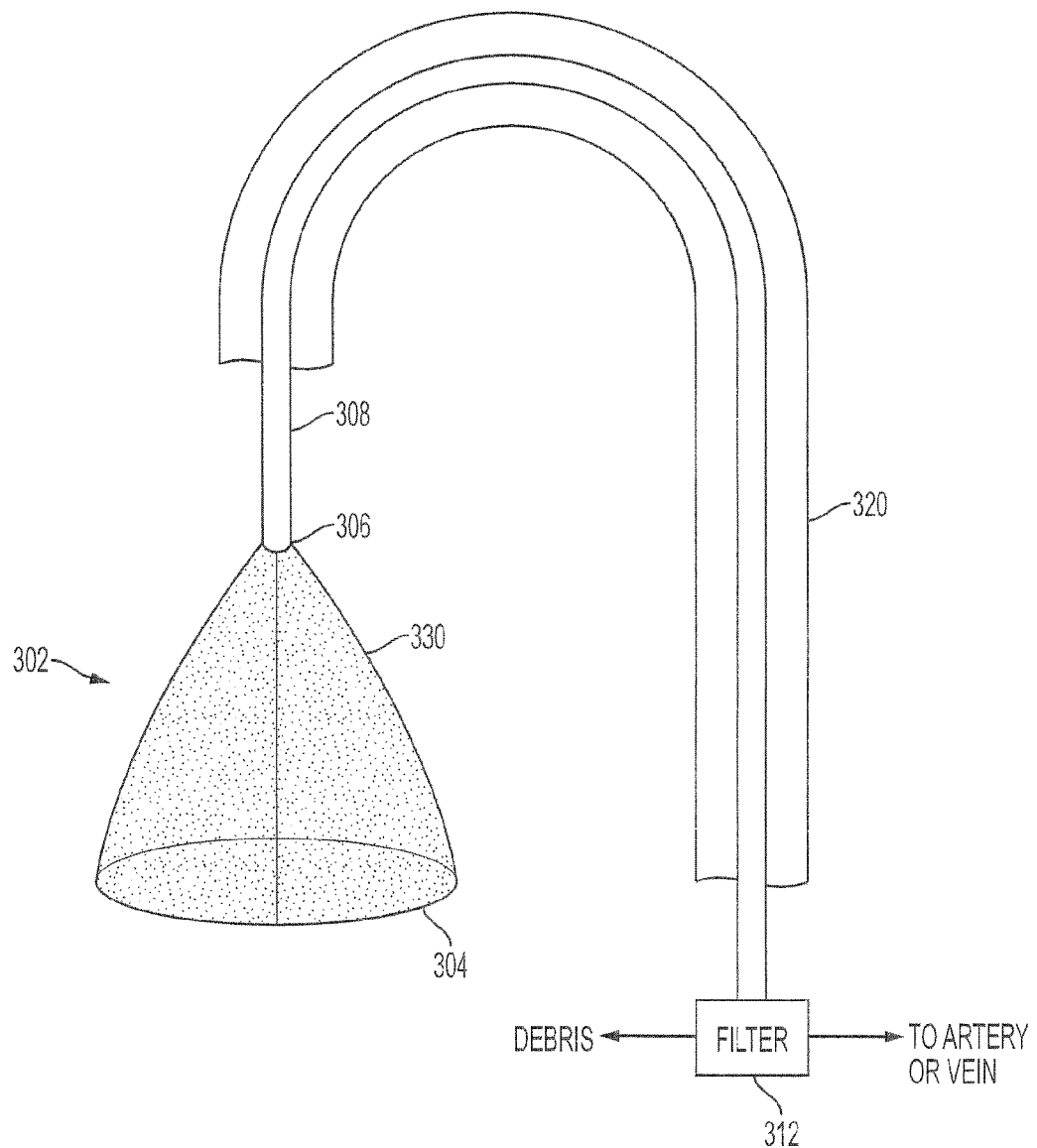
FIG. 12 is a pictorial view, partly in perspective and partly in cross section, of a further embodiment of the invention.

A further embodiment of a device incorporating a filter according to the present invention is illustrated in FIG. 12.

The embodiment shown in FIG. 12 is intended to be employed in connection with invasive procedures, such as open heart surgery, using instruments not introduced through, for example, the aorta.

A purpose of this embodiment is to avoid the adverse, and potentially fatal, effects of bypass surgery caused by the migration of emboli into the brain, resulting in strokes and cognitive disorders.

This embodiment includes a filter 302 that will be deployed at a location downstream of the surgical site. Filter 302 is somewhat similar in form to filter 2 shown in FIGS. 1 and 2 of the application drawing, filter 302 having a large diameter end 304 and a small diameter end 306, and the filter being opened, i.e. not provided with filter fabric, at both ends 304 and 306. Small diameter end 306 is secured to a suction tube 308.

Large diameter end 304 may have a deployed diameter of 32-40 mm, while small diameter end 306 and tube 308 may have a diameter of the order of 4 mm.

The proximal end of tube 308, i.e. the end that will be outside of the patient's body, is secured to a filter 312. The assembly composed of filter 302 and tube 308 may be introduced through a suitable sheath 320 into an artery to a point downstream of a location where debris will be produced by the surgical procedure and upstream of vessels that carry blood to the brain.

When filter 302 has been introduced to the desired location and deployed, and the surgical procedure is being performed, debris produced by the procedure will be conveyed, along with blood, into filter 302. A portion of the blood will then pass through the filter mesh, or fabric, that covers the circumference of filter 302 between ends 304 and 306 while the debris, along with some blood, will flow through small diameter end 306 and tube 308 to filter 312. In filter 312, debris will be separated from blood and the filtered blood may then be conducted into an artery or vein to be returned to the circulatory system. Filter 312 may be constructed according to principles already well known in the art.

The device shown in FIG. 12 may be introduced through any suitable artery. For example, in the case of open heart surgery, filter 302 may be introduced into the aorta along a path from an incision in the groin or through the subclavian artery.

Filter 302 could also be introduced on the right side of the heart in the pulmonary artery as potential means of preventing blood clots from entering the lungs and for right heart surgery. The device could be introduced in this case through a peripheral vein.

In all cases, filter 302 would be deployed downstream from the locations where emboli would be produced during the surgical procedure.

Figure 13:
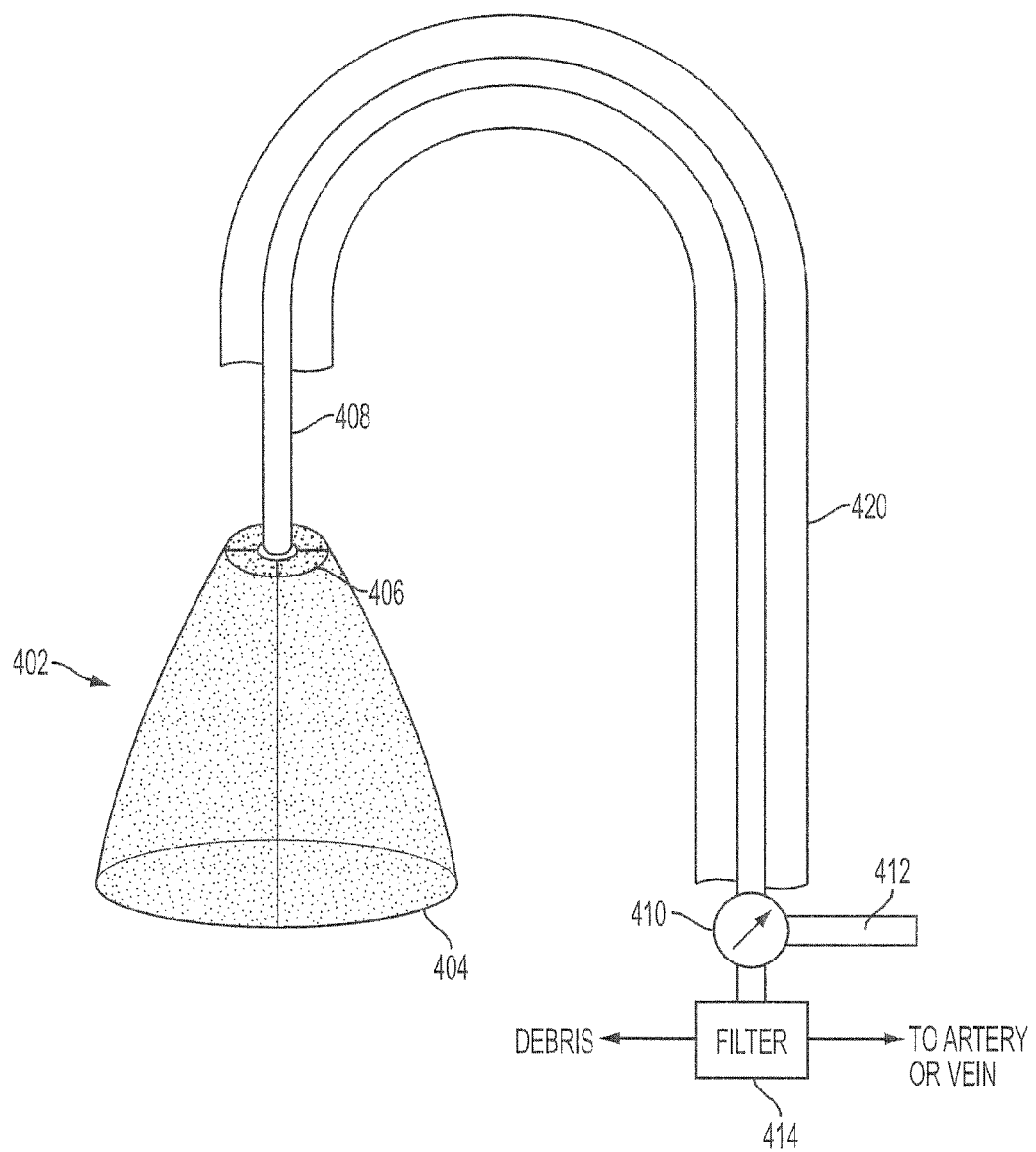
FIG. 13 is a pictorial view, partly in perspective and partly in cross section, of a further embodiment of the invention.

FIG. 13 shows a modified version of the device of FIG. 12 and embodies a filter 402 with an open end 404 at the bottom and an opening at the top 406, similar to that shown in FIG. 10, but without plate 160 and opening 162. The upper end 406 is closed by filter fabric material and has a central metal ring providing an orifice and spokes that connect the ring to the upper end of the filter. The orifice is not covered with filter fabric and allows the passage of a catheter 408 having a diameter of 5-7 Fr., and preferably 5-6 Fr., which can be introduced through a sheath 420 preliminarily passed through the radial artery with the aid of a guidewire, and then passed into the filter. This catheter 408, depending on what is needed, can either be a pigtail catheter or can be a fiberscope or an ultrasound device which can be used to view the aorta and the location of the valve and the walls of the aorta. Thus, this device can be used through its entrance sheath 420 in the arm to obtain pictorial representations of the condition of the aorta and the aortic valve, or other part being treated. This would be done prior to open heart surgery and could be replaced with a 5-7 F pigtail catheter, which is used to drain debris exiting from the apex of filter 402. The proximal end of catheter 408 will be attached, outside the patient's body, to a 3-way stop cock 410 through which contrast fluid can be introduced from a supply tube 412, or through which debris and blood could be passed to a filter 414, as described with reference to FIG. 12. This device will serve to minimize the spread of debris to the brain and body and enable blood flow to continue through 100 μm holes in the fabric.

The assembly shown in FIG. 13 differs from those used for TAVI, i.e, those involving introduction of a replacement heart valve through the arteries. Sheath 420 and tube 408 can be introduced through a subclavian artery, or a radial artery in the arm, or the groin. The exiting debris and blood is passed through an external filter and the blood is returned into the body as described in the case of the TAVI filter. This is different from the debris removal described TAVI procedures.

The assemblies shown in FIGS. 12 and 13 can be introduced via a femoral artery or a subclavian artery.

In all of the procedures employing filters according to the invention, any opposition to deployment and positioning of the filter can be minimized by temporarily halting or reducing the flow of blood from the aorta. This can be achieved, for example, by employing a pacemaker to produce a high pacing rate, for example of the order of 220 beats/minute.

While the description above refers to particular embodiments of the present invention, it will be understood that many modifications may be made without departing from the spirit thereof. The accompanying claims are intended to cover such modifications as would fall within the true scope and spirit of the present invention.

The present invention provides the possibility of using at most two entry passages to completely implant the filter, trap and withdraw debris and deploy an artificial valve. These entry points can be selected from one groin and the radial artery that leads into the subclavian to carry the pigtail catheter for introducing contrast fluid, or one groin, which carries the TAVI catheter and the sheath for implantation of the filter. In the event that the both groins are blocked and cannot be used, use can be made of one subclavian to deploy the filter and TAVI catheter and the other subclavian to introduce and advance the pigtail catheter. In either of these cases, the ability exists to perform two processes: To use the TAVI catheter and filter through a single groin or subclavian and the other to implant the pigtail catheter through the opposite groin or subclavian. In either case the ability to use the TAVI catheter with the filter depends on the ability to initially advance the filter with its sheath which encloses a guide wire, to deploy the filter and after this, to withdraw the sheath which surrounds the guidewire all the way to the origin of the point of insertion of the filter, thus, creating adequate space to advance the TAVI catheter with or without its own guide wire alongside this guidewire and to enter the orifice described in the filter.

However, if the TAVI catheter and filter were inserted into the right subclavian, it would still be possible to use the radial artery and subclavian of the left side to introduce the pigtail catheter and vice versa.

Filters according to the present invention can have a radial expansion ratio of 8:1. If the compressed diameter is, for example, 4.5 mm, the expanded filter can obturate the aorta with a lower ring such that it is inserted to apply pressure on the circumference of the aorta to stabilize it.

The catheter that may be a pigtail catheter can be used both for injecting contrast fluid for withdrawing debris from the filter in a safe and sterile way into an artery of the wrist, namely, the radial, which allows the observer to visually see the debris and subject it to quantitative and qualitative analysis and/or filtration. The debris can be analyzed by a cell counter such as a Coulter counter, which can enable a temporal estimation of debris production and clearance.

Relative to the use of a filter on the right side of the heart, it is possible to use a filter similar to the one described previously composed of nitinol and fabric and introduced through a sheath, which filter does not incorporate orifices, or openings, as previously described. This filter is introduced, enclosed by a sheath, through a vein which carries blood to the heart and which is located in an arm, the neck or the legs.

The sheath and filter can be introduced under fluoroscopic control into the right side of the heart, traversing one of the two main veins entering the heart and is manipulated under fluoroscopic control into the pulmonary artery which supplies the lungs. The filter is deployed in a similar manner by withdrawing the sheath and allowing it to stabilize in the pulmonary artery. Since the pulmonary artery divides into the left and right branch, these arteries to the left and right lung are protected from emboli. This technique is particularly applicable in cardiac surgery for congenital heart disease to prevent blood clots from entering the lungs, which is a known complication of this type of surgery. The filter is deployed and removed using the same techniques explained above with the TAVI filter and the other described filters, namely, by pulling the filter into a sheath to close it or expressing the filter out of the sheath, in deploying it.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A combination comprising:
    a collapsible and deployable filter for blocking debris and passing blood in a patient's aorta, said filter comprising:
        a framework of a flexible material, said framework being constructed to have a radially compressed state, in which said framework is radially compressed by radial deforming forces, and a radially expanded state; and
        a flexible filter material secured to said framework and having pores dimensioned to prevent the passage of debris therethrough while allowing the passage of blood, wherein:
        said filter has, in the radially expanded state of said framework, a generally conical or frustoconical form with a large diameter end, a small diameter end opposite to said large diameter end, and a side surface extending between said large diameter end and said small diameter end;
        said flexible filter material covers at least a major part of said side surface;
        said large diameter end is open to receive blood and debris and is dimensioned to prevent flow of blood and debris between said large diameter end and the aorta wall when said framework is in the radially expanded state;
        wherein said framework includes a circumferential ring at said large diameter end of said filter, said ring being constructed to have, in the radially expanded state of said framework, a circular or oval form, and
    said combination further comprises an assembly for implanting a prosthetic aortic valve in the patient's heart when said filter is deployed to block debris and pass blood ejected from the patient's heart, said assembly comprising a sheath or tube and a system enclosed by said sheath or tube and including the prosthetic heart valve;
        wherein said filter has a first opening that is free of filter material and is dimensioned to allow passage therethrough of said assembly for implanting a prosthetic aortic valve and to form a sealed connection with said sheath or tube, wherein said filter has a second opening that is free of filter material, and said device further comprises:
    a debris removal tube having a distal end dimensioned to have a close fit with said second opening for removal of debris collected in said filter, said debris removal tube having a proximal end and having a length sufficient to enable said proximal end to extend out of a patient's body when said filter is at a desired location in the blood vessel.

2. The combination of claim 1, further comprising:
    a second filter connected to said proximal end of said debris removal tube for separating debris conveyed through said debris removal tube from blood conveyed through said tube.

3. The combination of claim 2, further comprising:
    a source of contrast fluid connectable to said debris removal tube.

4. The combination of claim 3, further comprising a valve member installed in said debris removal tube in proximity to said proximal end of said debris removal tube, said valve member having a first operating state for placing said source of contrast fluid in fluid flow communication, through said debris removal tube, with the region enclosed by said filter and blocking flow to said second filter, and a second operating state placing the region enclosed by said filter in fluid flow communication, through said debris removal tube, with said second filter and blocking flow to and from said source of contrast fluid.

5. A procedure for removing debris from a blood vessel in a patient's body and allowing blood to pass through the blood vessel, comprising, in the order recited:
providing the combination according to claim 4;
introducing said filter into the blood vessel;
placing said valve member in the first operating state and passing contrast fluid from said source of contrast fluid through said debris removal tube; and
placing said valve member in the second operating state and causing debris to flow through said debris removal tube from the region enclosed by said filter to said second filter.

6. The procedure of claim 5, further comprising passing blood that has been separated from the debris in said second filter to a second blood vessel.

7. Apparatus for removing debris from blood flowing through a blood vessel, comprising:
the combination according to claim 1; and
a debris removal device operative to extend into the space enclosed by said filter and to conduct debris from the space enclosed by said filter to a location outside the patient's body.

8. A procedure for implanting a prosthetic aortic valve in the patient's heart while blocking flow of debris through the aorta, comprising:
providing the combination of claim 7,
inserting said filter, in its radially compressed state in said sheath, along a blood vessel path into the aorta;
withdrawing said sheath to cause said filter to assume the radially expanded state at a desired location on the aorta;
inserting said assembly for implanting a prosthetic aortic valve in the patient's heart into the aorta through said opening of said filter, and through said large diameter end of said filter and past an existing heart valve;
operating said assembly to implant the prosthetic aortic valve;
conveying debris resulting from said inserting and operating steps, with said debris removal device, from the region enclosed by said filter to a location outside the patient's body; and
withdrawing said assembly from the patient's body.

9. The procedure of claim 8, further comprising supplying contrast medium to the location where the valve is implanted.

10. The procedure of claim 9, wherein the contrast medium is supplied through the debris removal device.

11. The apparatus of claim 7, wherein said first opening is at said small diameter end of said filter, and said second opening that is free of filter material is in said side surface, and said debris removal device comprises a debris removal tube having a distal end communicating with the region enclosed by said filter through said second opening and dimensioned to have a proximal end that extends out of the patient's body when said filter is in the desired location in a blood vessel.

12. The combination of claim 1, wherein said first opening is at said small diameter end of said filter, and is dimensioned to allow passage of said assembly for implanting a prosthetic aortic valve in the patient's heart through said first opening at said small diameter end.

13. The combination of claim 12, further comprising at least one control wire having a distal end connected to said framework at the small diameter end of said filter.

14. A device for removing debris from a blood vessel, comprising:
the combination according to claim 13; and
a sheath having an internal diameter selected to house said filter in the radially compressed state, said sheath having a length sufficient to extend out of a patient's body when said filter is at a desired location in a blood vessel at said small diameter end of said filter.

15. A combination comprising:
a collapsible and deployable filter for blocking debris and passing blood in a patient's aorta, said filter comprising:
a framework of a flexible material, said framework being constructed to have a radially compressed state, in which said framework is radially compressed by radial deforming forces, and a radially expanded state; and
a flexible filter material secured to said framework and having pores dimensioned to prevent the passage of debris therethrough while allowing the passage of blood, wherein:
said filter has, in the radially expanded state of said framework, a generally conical or frustoconical form with a large diameter end, a small diameter end opposite to said large diameter end, and a side surface extending between said large diameter end and said small diameter end;
said flexible filter material covers at least a major part of said side surface;
said large diameter end is open to receive blood and debris and is dimensioned to prevent flow of blood and debris between said large diameter end and the aorta wall when said framework is in the radially expanded state; and
said filter has a first opening that is free of filter material in said side surface; and
an assembly for implanting a prosthetic aortic valve in the patient's heart when said filter is deployed to block debris and pass blood ejected from the patient's heart, said first opening that is free of filter material in said side surface being dimensioned to allow passage of said assembly through said opening; and
further comprising a closing member secured in said first opening to normally close said first opening, wherein said closing member is composed of a series of flaps.

16. The combination of claim 15, further comprising an entry cone that extends into said filter from said first opening to guide insertion of said assembly for implanting a prosthetic aortic valve into the region enclosed by said filter when said filter is in the radially expanded state.

17. The combination of claim 16, wherein said cone has an inner end dimensioned to form a seal with said assembly for implanting a prosthetic aortic valve.

18. The combination of claim 15, wherein:
said filter has a second opening that is free of filter material in said side surface; and
said combination further comprises a tube having a distal end communicating with the region enclosed by said filter and insertable through said second opening and dimensioned to have a proximal end that extends out of the patient's body when said filter is in the desired location in a blood vessel, to inject contrast fluid into the region of the aortic valve when said filter is in the radially expanded state.

\* \* \* \* \*